(12) United States Patent
Katagiri et al.

(10) Patent No.: US 7,815,895 B2
(45) Date of Patent: Oct. 19, 2010

(54) METHOD FOR ACTIVATING EFFERENT SYMPATHETIC NERVES INNERVATING ADIPOSE TISSUES TO IMPROVE OBESITY AND SYMPTOMS ASSOCIATED THEREWITH

(75) Inventors: Hideki Katagiri, Sendai (JP); Yoshitomo Oka, Sendai (JP); Tetsuya Yamada, Sendai (JP); Kenji Uno, Sendai (JP)

(73) Assignee: Tohoku University, Miyagi (JP)

( * ) Notice: Subject to any disclaimer, the term of this patent is extended or adjusted under 35 U.S.C. 154(b) by 60 days.

(21) Appl. No.: 11/751,144

(22) Filed: May 21, 2007

(65) Prior Publication Data

US 2008/0293830 A1 Nov. 27, 2008

(51) Int. Cl.
*A61K 49/00* (2006.01)
*G01N 33/567* (2006.01)
*C12N 5/10* (2006.01)
*C12N 5/02* (2006.01)

(52) U.S. Cl. ........................ 424/9.2; 435/7.21; 435/391; 435/69.1

(58) Field of Classification Search ........................ None
See application file for complete search history.

(56) References Cited

OTHER PUBLICATIONS

Eisen S et al. Inhibitory effects on intake of cholecystokinin-8 and cholecystokinin-33 in rats with hepatic proper or common hepatic branch vagal innervation. Am J Physiol Regul Integr Comp Physiol. 2005; 289:R456-R462.*
Horn CC et al. Role of vagal afferent innervation in feeding and brain Fos expression produced by metabolic inhibitors. Brain Res. 2001; 919:198-206.*
Kim S et al. Hepatic gene expression profiles in a long-term high-fat diet-induced obesity mouse model. Gene, Sep. 2004; 340(1):99-109.*
Nakano R et al. Antagonism of peroxisome proliferator-activated receptor gamma prevents high-fat diet-induced obesity in vivo. Biochem Pharmacol. Jun. 2006; 72:42-52.*
Flier, J.S., "Obesity Wars: Molecular Progress Confronts an Expanding Epidemic", Cell, vol. 116, Jan. 23, 2004, pp. 337-350.
Friedman, J.M. et al., "Leptin and the regulation of body weight in mammals", Nature, vol. 395, Oct. 22, 1998, pp. 763-770.
Minokoshi, Yasuhiko et al., "Tissue-specfic Ablation of the GLUT4 Glucose Transporter or the Insulin Receptor Challenges Assumptions about Insulin Action and Glucose Homeostasis", The Journal of Biological Chemistry, vol. 278, Sep. 5, 2003, pp. 33609-33612.
Kitamura, Tadahiro et al., "Insulin Receptor Knockout Mice", Annual Review of Physiology, vol. 65, 2003, pp. 313-332.
An, Jie et al., "Hepatic expression of malonyl-CoA decarboxylase reverses muscle, liver and whole-animal insulin resistance", Nature Medicine, Feb. 8, 2004, pp. 1-7.
Yamada, Tetsuya et al., "Signals from intra-abdominal fat modulate insulin and leptin sensitivity through different mechanisms: Neuronal involvement in food-intake regulation", Cell Metabolism, vol. 3, Mar. 2006, pp. 223-229.

Gavrilova, Oksana et al., "Liver Peroxisome Proliferator-activated Receptor γ Contributes to Hepatic Steatosis, Triglyceride Clearance, and Regulation of Body Fat Mass", The Journal of Biological Chemistry, vol. 276, Sep. 5, 2003, pp. 34268-34276.
Bocher, Virginie et al., "PPARs: Transcription Factors Controlling Lipid and Lipoprotein Metabolism", Annals of the New York Academy of Sciences, vol. 967, 2002, pp. 7-18.
Fajas, Lluis et al., "The Organization, Promoter Analysis, and Expression of the Human PPARγ Gene", The Journal of Biological Chemistry, vol. 272, No. 30, Jul. 25, 1997, pp. 18779-18789.
Burant, Charles F. et al., "Troglitazone Action is Independent of Adipose Tissue", The Journal of Clinical Investigation, vol. 100, No. 11, Dec. 1997, pp. 2900-2908.
Chao, Lily et al., "Adipose tissue is required for the antidiabetic, but not for the hypolipidemic, effect of thiazolidinediones", The Journal of Clinical Investigation, vol. 106, No. 10, Nov. 2000, pp. 1221-1228.
Rahimian, Roshanak et al., "Hepatic over-expression of peroxisome proliferator activated receptor γ2 in the ob/ob mouse model of non-insulin dependent diabetes mellitus", Molecular and Cellular Biochemistry, vol. 224, Apr. 9, 2001, pp. 29-37.
Matsusue, Kimihiko et al., "Liver-specific disruption of PPARγ in leptin-deficient mice improves fatty liver but aggravates diabetic phenotypes", The Journal of Clinical Investigation, vol. 111, No. 5, Mar. 2003, pp. 737-747.
Ishigaki, Yasushi et al., "Dissipating Excess Energy Stored in the Liver is a Potential Treatment Strategy for Diabetes Associated With Obesity", Perspectives in Diabetes, vol. 54, Feb. 2005, pp. 322-332.
Hosono, Tetsuji et al., "RNA interference of PPARγ using fiber-modified adenovirus vector efficiently suppresses preadipocyte-to-adipocyte differentiation in 3T3-L1 cells", Gene Section Functional Genomics, vol. 348, 2005, pp. 157-165.
Katagiri, Hideki et al., "Overexpression of Catalytic Subunit P110α of Phosphatidylinositol 3-Kinase Increases Glucose Transport Activity with Translocation of Glucose Transporters in 3T3-L1 Adipocytes", The Journal of Biological Chemistry, vol. 271, No. 29, Jul. 19, 1996, pp. 16987-16990.
Kanegae, Yumi et al., "Efficient gene activation in mammalian cells by using recombinant adenovirus expressing site-specific Cre recombinase", Nucleic Acids Research, vol. 23, No. 19, pp. 3816-3821.
Ikemoto, Shinji et al., "High fat diet-induced hyperglycemia: Prevention by low level expression of a glucose transporter (GLUT4) minigene in transgenic mice", Proceedings of the National Academy of Sciences of the United States of America, vol. 92, Apr. 1995, pp. 3096-3099.

(Continued)

*Primary Examiner*—Elizabeth C. Kemmerer
*Assistant Examiner*—Kimberly A. Ballard
(74) *Attorney, Agent, or Firm*—Barnes & Thornburg LLP

(57) ABSTRACT

A method for activating an efferent sympathetic nerve innervating an adipose tissue and improving obesity-associated symptoms is provided, comprising stimulating an afferent vagal nerve from the liver without directly enhancing peroxisome proliferator-activated receptor (PPAR)-γ2 function in the liver.

4 Claims, 10 Drawing Sheets

OTHER PUBLICATIONS

Ono, Hiraku et al., "Hepatic Akt Activation Induces Marked Hypoglycemia, Hepatomegaly, and Hypertriglyceridemia With Sterol Regulatory Element Binding Protein Involvement", Diabetes, vol. 52, Dec. 2003, pp. 2905-2913.

Ogihara, Takehide et al., "Insulin Receptor Substrate (IRS)-2 Is Dephosphorylated More Rapidly than IRS-1 via Its Association with Phosphatidylinositol 3-Kinase in Skeletal Muscle Cells", The Journal of Biological Chemistry, vol. 272, No. 19, May 9, 1997, pp. 12868-12873.

Jones, Julie R. et al., "Deletion of PPARγ in adipose tissues of mice protects against high fat diet-induced obesity and insulin resistance", Proceedings of the National Academy of Sciences of the United States of America, vol. 102, No. 17, Apr. 26, 2005, pp. 6207-6212.

Nashat, Amir H. et al., "Temporal Characteristics of Activation, Deactivation, and Restimulation of Signal Transduction following Depolarization in the Pheochromocytoma Cell Line PC12", Molecular and Cellular Biology, vol. 23, No. 14, Jul. 2003, pp. 4788-4795.

* cited by examiner

A

B

C

SEQUENCE LISTING

<160> NUMBER OF SEQ ID NOS: 44

<210> SEQ ID NO 1
<211> LENGTH: 24
<212> TYPE: DNA
<213> ORGANISM: Mus musculus

<400> SEQUENCE: 1
ttgtaaccaa ctgggacgat atgg                24

```
<210> SEQ ID NO 2
<211> LENGTH: 24
<212> TYPE: DNA
<213> ORGANISM: Mus musculus

<400> SEQUENCE: 2
gatcttgatc ttcatggtgc tagg                                              24

<210> SEQ ID NO 3
<211> LENGTH: 18
<212> TYPE: DNA
<213> ORGANISM: Mus musculus

<400> SEQUENCE: 3
agcggatatg gtgggaac                                                     18

<210> SEQ ID NO 4
<211> LENGTH: 18
<212> TYPE: DNA
<213> ORGANISM: Mus musculus

<400> SEQUENCE: 4
ggtctccact ccttgttc                                                     18

<210> SEQ ID NO 5
<211> LENGTH: 22
<212> TYPE: DNA
<213> ORGANISM: Mus musculus

<400> SEQUENCE: 5
ataccgcaaa gagcacgaga ag                                                22

<210> SEQ ID NO 6
<211> LENGTH: 25
<212> TYPE: DNA
<213> ORGANISM: Mus musculus

<400> SEQUENCE: 6
ctcaagagca gcgaaagcgt cacag                                             25

<210> SEQ ID NO 7
<211> LENGTH: 18
<212> TYPE: DNA
<213> ORGANISM: Mus musculus

<400> SEQUENCE: 7
taccaagctg tgcgatgt                                                     18

<210> SEQ ID NO 8
<211> LENGTH: 19
<212> TYPE: DNA
<213> ORGANISM: Mus musculus

<400> SEQUENCE: 8
aagcccaatg atgttcagt                                                    19

<210> SEQ ID NO 9
<211> LENGTH: 21
<212> TYPE: DNA
<213> ORGANISM: Mus musculus

<400> SEQUENCE: 9
tggttcaact ggagagcgga t                                                 21
```

```
<210> SEQ ID NO 10
<211> LENGTH: 21
<212> TYPE: DNA
<213> ORGANISM: Mus musculus

<400> SEQUENCE: 10
tgatgcagag attcccacct g                                        21

<210> SEQ ID NO 11
<211> LENGTH: 18
<212> TYPE: DNA
<213> ORGANISM: Mus musculus

<400> SEQUENCE: 11
agggaatgag gagcagcc                                            18

<210> SEQ ID NO 12
<211> LENGTH: 18
<212> TYPE: DNA
<213> ORGANISM: Mus musculus

<400> SEQUENCE: 12
gttcttcagc cgccagtt                                            18

<210> SEQ ID NO 13
<211> LENGTH: 21
<212> TYPE: DNA
<213> ORGANISM: Mus musculus

<400> SEQUENCE: 13
tggctaaatg agactgggac c                                        21

<210> SEQ ID NO 14
<211> LENGTH: 22
<212> TYPE: DNA
<213> ORGANISM: Mus musculus

<400> SEQUENCE: 14
acatcaccac tccaatccca ag                                       22

<210> SEQ ID NO 15
<211> LENGTH: 19
<212> TYPE: DNA
<213> ORGANISM: Mus musculus

<400> SEQUENCE: 15
agggtcgaat tgggatggc                                           19

<210> SEQ ID NO 16
<211> LENGTH: 18
<212> TYPE: DNA
<213> ORGANISM: Mus musculus

<400> SEQUENCE: 16
gggtcacttt gcggtgtt                                            18

<210> SEQ ID NO 17
<211> LENGTH: 21
<212> TYPE: DNA
<213> ORGANISM: Mus musculus

<400> SEQUENCE: 17
cttctacttt caagaccgcc t                                        21
```

<210> SEQ ID NO 18
<211> LENGTH: 21
<212> TYPE: DNA
<213> ORGANISM: Mus musculus

<400> SEQUENCE: 18
ggcacaccat agacattgac t                                          21

<210> SEQ ID NO 19
<211> LENGTH: 20
<212> TYPE: DNA
<213> ORGANISM: Mus musculus

<400> SEQUENCE: 19
catggattgc acatttgaag                                            20

<210> SEQ ID NO 20
<211> LENGTH: 18
<212> TYPE: DNA
<213> ORGANISM: Mus musculus

<400> SEQUENCE: 20
cctgtgtccc ctgtctca                                              18

<210> SEQ ID NO 21
<211> LENGTH: 21
<212> TYPE: DNA
<213> ORGANISM: Mus musculus

<400> SEQUENCE: 21
tcgaaagcgg ctcacaagca g                                          21

<210> SEQ ID NO 22
<211> LENGTH: 21
<212> TYPE: DNA
<213> ORGANISM: Mus musculus

<400> SEQUENCE: 22
caccgcagct ttccggaatg t                                          21

<210> SEQ ID NO 23
<211> LENGTH: 17
<212> TYPE: DNA
<213> ORGANISM: Mus musculus

<400> SEQUENCE: 23
tgctcccagc tgcaggc                                               17

<210> SEQ ID NO 24
<211> LENGTH: 20
<212> TYPE: DNA
<213> ORGANISM: Mus musculus

<400> SEQUENCE: 24
gcccggtagc tctgggtgta                                            20

<210> SEQ ID NO 25
<211> LENGTH: 17
<212> TYPE: DNA
<213> ORGANISM: Mus musculus

<400> SEQUENCE: 25
tgggttggct gcttgtg                                                   17

<210> SEQ ID NO 26
<211> LENGTH: 17
<212> TYPE: DNA
<213> ORGANISM: Mus musculus

<400> SEQUENCE: 26
gcgtgggcag gatgaag                                                   17

<210> SEQ ID NO 27
<211> LENGTH: 21
<212> TYPE: DNA
<213> ORGANISM: Mus musculus

<400> SEQUENCE: 27
atgcaagagc ttccacagga a                                              21

<210> SEQ ID NO 28
<211> LENGTH: 20
<212> TYPE: DNA
<213> ORGANISM: Mus musculus

<400> SEQUENCE: 28
cagaaatcgc caactcagca                                                20

<210> SEQ ID NO 29
<211> LENGTH: 24
<212> TYPE: DNA
<213> ORGANISM: Mus musculus

<400> SEQUENCE: 29
cattctgacc atggtgcgta ctga                                           24

<210> SEQ ID NO 30
<211> LENGTH: 24
<212> TYPE: DNA
<213> ORGANISM: Mus musculus

<400> SEQUENCE: 30
gttcatgtat ctcgtcttga ccac                                           24

<210> SEQ ID NO 31
<211> LENGTH: 23
<212> TYPE: DNA
<213> ORGANISM: Mus musculus

<400> SEQUENCE: 31
ggatgtcaca caatgcaatt cgc                                            23

<210> SEQ ID NO 32
<211> LENGTH: 22
<212> TYPE: DNA
<213> ORGANISM: Mus musculus

<400> SEQUENCE: 32
tcacagaacg gcttcctcag gt                                             22

<210> SEQ ID NO 33
<211> LENGTH: 20
<212> TYPE: DNA
<213> ORGANISM: Mus musculus

<400> SEQUENCE: 33
aacgcaccct ttgtcatcca                                          20

<210> SEQ ID NO 34
<211> LENGTH: 19
<212> TYPE: DNA
<213> ORGANISM: Mus musculus

<400> SEQUENCE: 34
tttccacacc aggcccttc                                           19

<210> SEQ ID NO 35
<211> LENGTH: 21
<212> TYPE: DNA
<213> ORGANISM: Mus musculus

<400> SEQUENCE: 35
gaattcgatg aaatcaccgc a                                        21

<210> SEQ ID NO 36
<211> LENGTH: 24
<212> TYPE: DNA
<213> ORGANISM: Mus musculus

<400> SEQUENCE: 36
ctctttattg tggtcgactt tcca                                     24

<210> SEQ ID NO 37
<211> LENGTH: 20
<212> TYPE: DNA
<213> ORGANISM: Mus musculus

<400> SEQUENCE: 37
ggatagggtt ggagtcagca                                          20

<210> SEQ ID NO 38
<211> LENGTH: 20
<212> TYPE: DNA
<213> ORGANISM: Mus musculus

<400> SEQUENCE: 38
cttgccgctt cagtttcttc                                          20

<210> SEQ ID NO 39
<211> LENGTH: 22
<212> TYPE: DNA
<213> ORGANISM: Mus musculus

<400> SEQUENCE: 39 tttttttgaaa tgtgcgccag tc                                      22

<210> SEQ ID NO 40
<211> LENGTH: 22
<212> TYPE: DNA
<213> ORGANISM: Mus musculus

<400> SEQUENCE: 40
agcacgtaat accgagtgag at                                       22

<210> SEQ ID NO 41
<211> LENGTH: 20
<212> TYPE: DNA
<213> ORGANISM: Mus musculus

```
<400> SEQUENCE: 41
accagcgcca cttcttcacg                                              20

<210> SEQ ID NO 42
<211> LENGTH: 20
<212> TYPE: DNA
<213> ORGANISM: Mus musculus

<400> SEQUENCE: 42
gtggagcatc atactgatcc                                              20

<210> SEQ ID NO 43
<211> LENGTH: 18
<212> TYPE: DNA
<213> ORGANISM: Mus musculus

<400> SEQUENCE: 43
cgctgatgca ctgcctat                                                18

<210> SEQ ID NO 44
<211> LENGTH: 20
<212> TYPE: DNA
<213> ORGANISM: Mus musculus

<400> SEQUENCE: 44
agaggtccac agagctgatt                                              20
```

METHOD FOR ACTIVATING EFFERENT SYMPATHETIC NERVES INNERVATING ADIPOSE TISSUES TO IMPROVE OBESITY AND SYMPTOMS ASSOCIATED THEREWITH

TECHNICAL FIELD

The present invention relates to methods for activating efferent sympathetic nerves innervating adipose tissues to improve obesity and obesity-associated symptoms.

DESCRIPTION OF THE RELATED ART

The incidence of obesity, insulin resistance, hyperlipidemia and hypertension, collectively termed the metabolic syndrome, is increasing at an alarming rate in Western cultures (J. S. Flier, Cell 116, 337 (2004)). Secreted humoral factors, including leptin (J. M. Friedman, J. L. Halaas, Nature 395, 763 (1998)), convey information about energy storage from adipose tissue to the central nervous system. As in adipose tissues, fat storage in the liver is dynamically changed by overall energy balance, but our understanding of how the liver transmits metabolic signals to other tissues remains incomplete.

Studies of mouse models created by tissue-specific gene-engineering (Y. Minokoshi, C. R. Kahn, B. B. Kahn, J Biol Chem 278, 33609 (2003); T. Kitamura, C. R. Kahn, D. Accili, Annu Rev Physiol 65, 313 (2003)) or adenoviral gene transfer (J. An et al., Nat Med 10, 268 (2004); T. Yamada et al., Cell Metab 3, 223 (2006)) have shown the importance of cross-talk between tissues in the regulation of energy metabolism. Mice with tissue-specific knockout of peroxisome proliferator-activated receptor γ (PPARγ) provide an example of such inter-tissue communication (O. Gavrilova et al., J Biol Chem 278, 34268 (2003)). PPARγ activates genes involved in lipid storage and metabolism (V. Bocher, I. Pineda-Torra, J. C. Fruchart, B. Staels, Ann NY Acad Sci 967, 7 (2002)). Although PPARγ expression in the liver is low compared with that in adipose tissues (L. Fajas et al., J Biol Chem 272, 18779 (1997)), hepatic expression of PPARγ (C. F. Burant et al., J Clin Invest 100, 2900 (1997); L. Chao et al., J Clin Invest 106, 1221 (2000)), especially PPARγ2 (R. Rahimian et al., Mol Cell Biochem 224, 29 (2001)), is functionally enhanced in a number of obesity models. In addition, liver-specific disruption of PPARγ in ob/ob mice prevents hepatic steatosis, but increases peripheral adiposity and decreases insulin sensitivity in muscle and fat (K. Matsusue et al., J Clin Invest 111, 737 (2003)). Thus, hepatic PPARγ2 plays important roles not only in the development of liver steatosis, but also in the regulation of peripheral lipid storage and insulin sensitivity.

Taking advantage of adenovirus gene transfer, PPARγ2 was overexpressed specifically in the liver of mice that have been fed by a high-fat food. The phenotypic analyses of the mice (PPARγ2-mice) have uncovered an interaction between the liver and adipose tissue. In the PPARγ2 mice, liver weights were increased due to increased triglyceride content, while white adipose tissue (WAT) was remarkably diminished in size. Cell diameters in WAT and brown adipose tissue (BAT) were also markedly decreased. The increases in body weights induced by a high fat diet were suppressed in the PPARγ2-mice. Systemic energy expenditure was found to increase, which should be a reason why their body weights were suppressed.

The overexpression of PPARγ2 in the liver was thus shown to lead to increase of the liver weight and systemic energy expenditure and decrease of adipose tissues. However, the mechanism was totally unknown.

SUMMARY OF THE INVENTION

One aspect of the present invention is directed to a method for activating an efferent sympathetic nerve innervating an adipose tissue. This method comprises stimulating an afferent vagal nerve from the liver without directly enhancing peroxisome proliferator-activated receptor (PPAR)-γ2 function in the liver.

Another aspect of the present invention is directed to a method for diminishing an adipose tissue. This method comprises stimulating an afferent vagal nerve from the liver without directly enhancing PPARγ2 function in the liver. In one embodiment, the adipose tissue is a white adipose tissue (WAT) and/or a brown adipose tissue (BAT).

Another aspect of the present invention is directed to a method for increasing systemic energy expenditure. This method comprises stimulating an afferent vagal nerve from the liver without directly enhancing PPARγ2 function in the liver.

Another aspect of the present invention is directed to a method for suppressing weight gain or obesity. This method comprises stimulating an afferent vagal nerve from the liver without directly enhancing PPARγ2 function in the liver.

Another aspect of the present invention is directed to a method for improving an obesity-associated symptom. The obesity-associated symptom may be selected from the group consisting of diabetes, hyperglycemia, glucose intolerance, and insulin resistance. This method comprises stimulating an afferent vagal nerve from the liver without directly enhancing PPARγ2 function in the liver.

A further aspect of the present invention is directed to a method for screening for a substance for weight reduction, and/or improving an obesity-associated symptom. The obesity-associated symptom may be selected from the group consisting of diabetes, hyperglycemia, glucose intolerance, and insulin resistance. This method comprises screening for a substance that excites an afferent vagal nerve from the liver. In one embodiment, the substance is derived from culture supernatant of a hepatocyte in which PPARγ2 is overexpressed.

(A-B) Immunoblotting with anti-PPARγ antibody of liver (A) and epididymal fat (B) extracts. (C-D) Liver weight (C) and triglyceride content (D). (E) Epididymal fat tissue weights. Experiments in (A)-(E) were performed on day 7 after adenoviral administration. (F) Body weight changes during the 7 days after adenoviral administration. (G) Resting oxygen consumption (VO2) was measured on day 3 after adenoviral injection. (H) Total food intake was measured for 7 days after adenoviral administration. LacZ-mice: white bars, PPARγ2-mice: black bars. **P<0.01 and *P<0.05, compared to LacZ-mice, by unpaired t test.

Figure 2:
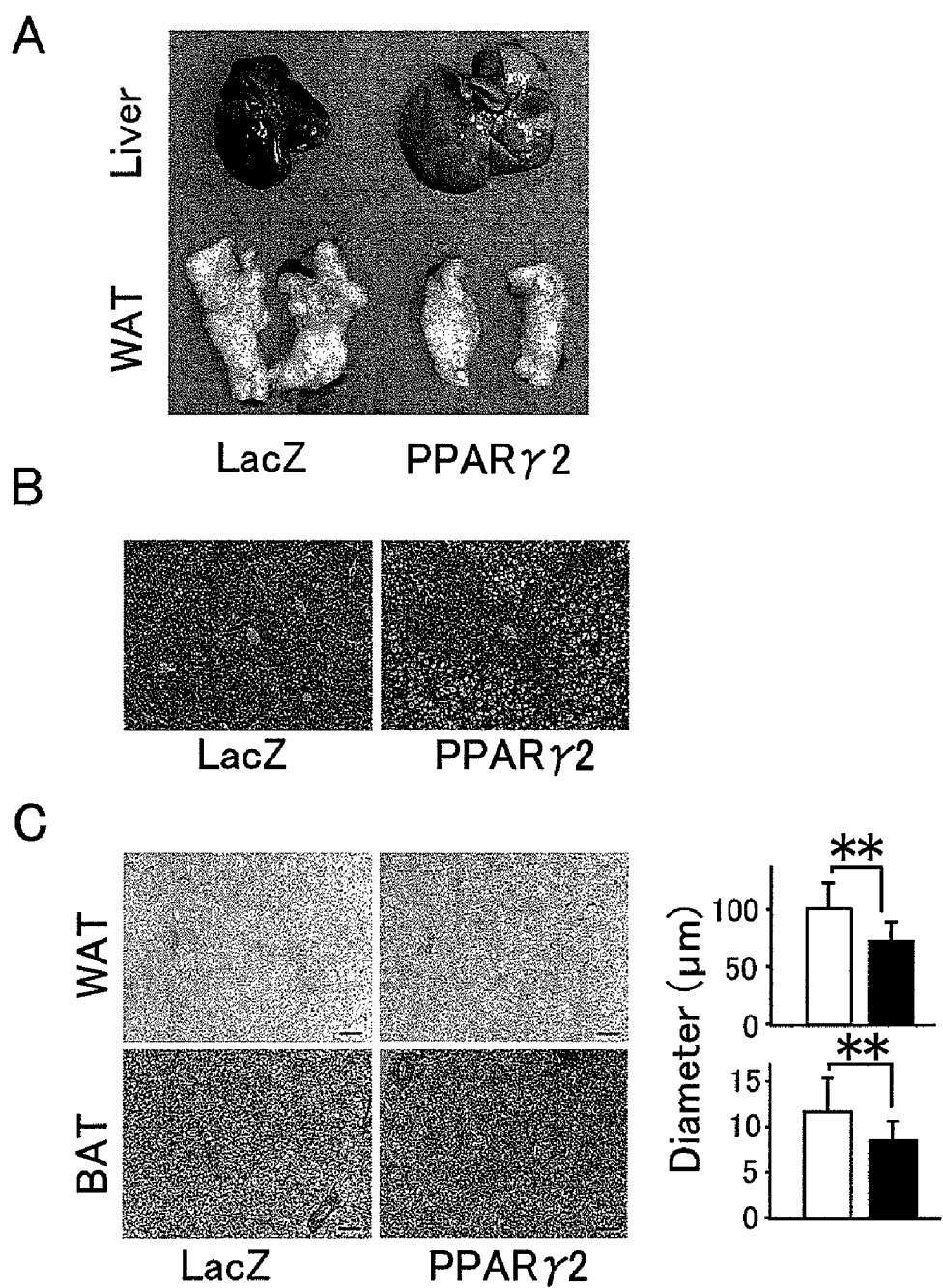

FIG. 2 shows aggravated hepatic steatosis and diminished peripheral adiposity, due to hepatic PPARγ2 expression in an example. (A) Appearances of liver and epididymal fat tissue from LacZ-mice and PPARγ2-mice. (B) Histological findings with hematoxylin eosin (HE) staining of the liver. (C) Histological findings with HE staining of epididymal fat (upper panels) and brown adipose tissue (lower panels) in LacZ-mice and PPARγ2-mice. The scale bars indicate 100 μm. Diameters of adipocytes are presented graphically (right panels) in LacZ-mice (white bars) and PPARγ2-mice (black bars). Cell diameters of at least 150 adipocytes per mouse in each group were traced manually and analyzed. Experiments were performed on day 7 after adenoviral administration. Data are presented as mean±SD. **P<0.01, compared to control mice, by unpaired t test.

Figure 3:
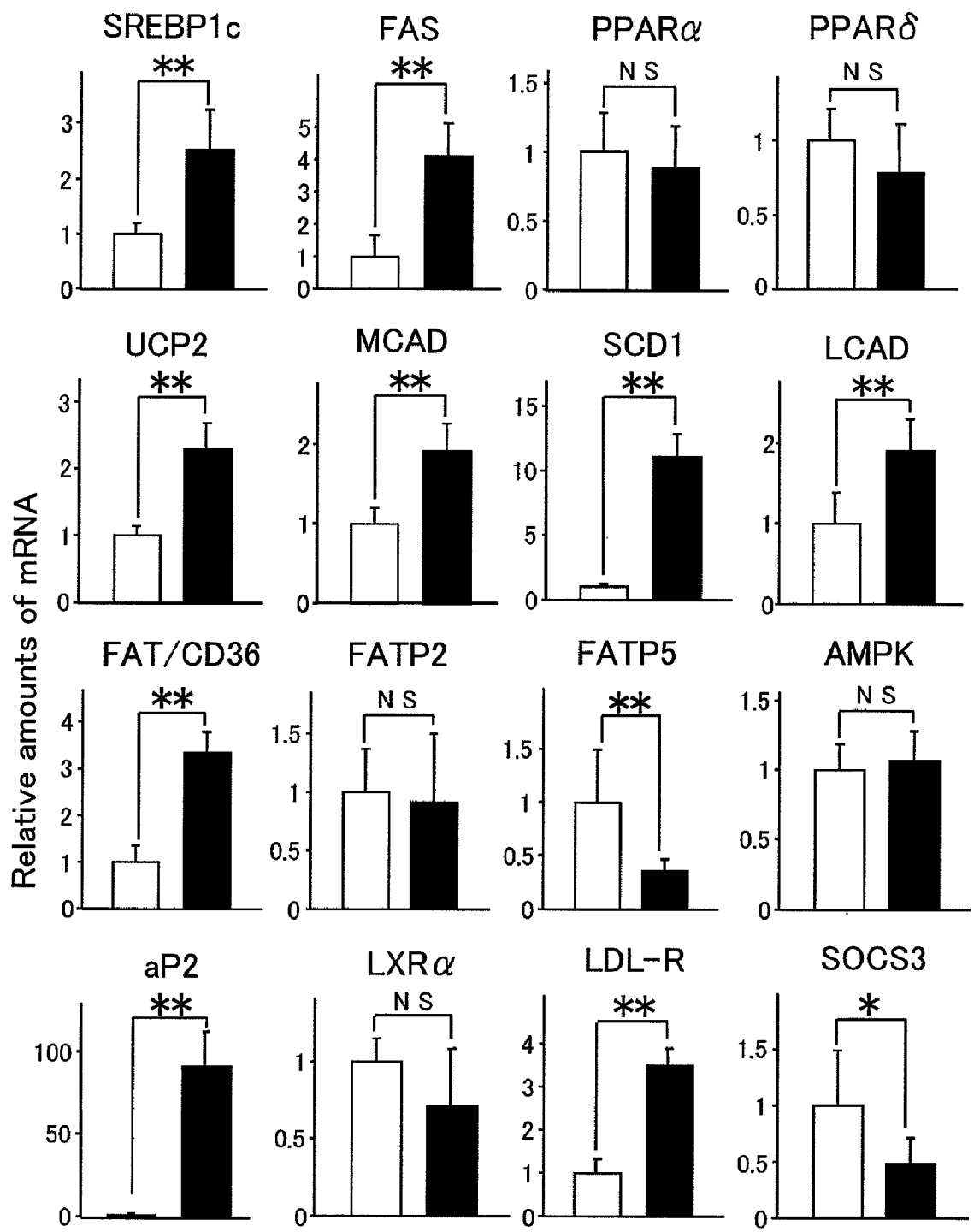

FIG. 3 shows relative amounts of mRNAs of hepatic proteins from LacZ-(white bars) and PPARγ2-(black bars) mice on day 7 after adenoviral administration in an example. Data are presented as mean±SD. **P<0.01 and *P<0.05, compared to LacZ-mice, by unpaired t test.

Figure 4:
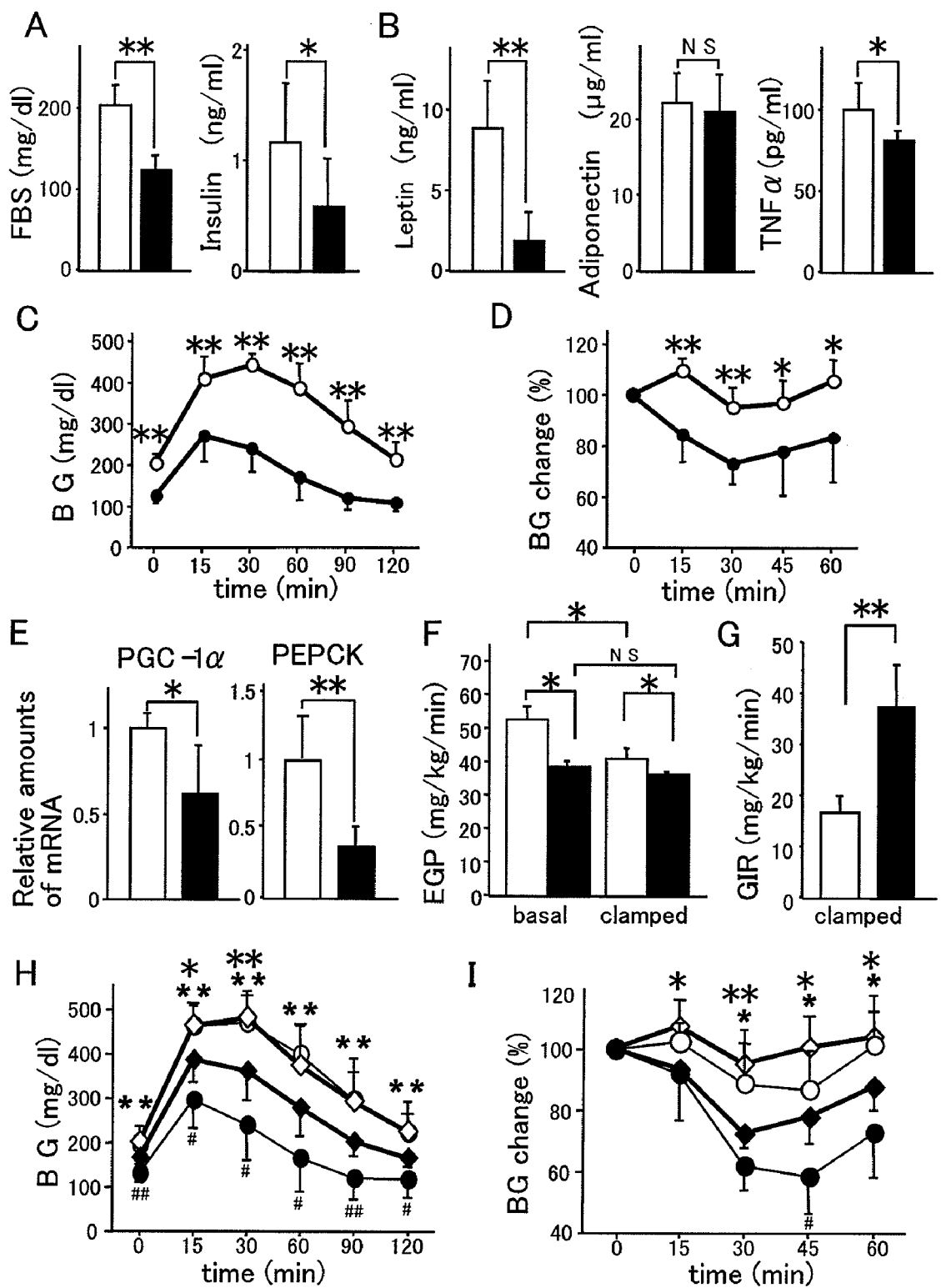

FIG. 4 shows improved peripheral insulin resistance due to hepatic PPARγ2 expression in an example.

(A-B) Fasting blood glucose and serum insulin (A), and adipocytokines (B) were measured in LacZ-mice (white bars) and PPARγ2-mice (black bars) on day 7 after adenoviral administration. These serum parameters were measured after a 10 hour fast. (C-D) LacZ-mice (open circle) and PPARγ2-mice (closed circle) were subjected to glucose-tolerance (C) and insulin-tolerance (D) tests. (E) Relative amounts of PGC-1α and PEPCK mRNA in the liver were measured by quantitative RT-PCR. (F-G) Metabolic variables during hyperinsulinemic euglycemic clamp. Endogenous glucose production in basal and clamped states (F) and rates of glucose infusion required to maintain euglycemia during the clamp study (G). Experiments in (A)-(G) were performed on day 7 after adenoviral administration. LacZ-mice: white bars, PPARγ2-mice: black bars. **P<0.01 and *P<0.05, compared to LacZ-mice, by unpaired t test. (H-I) Hepatic vagotomy (HV) or sham operation (SO) was performed 7 days prior to administration of LacZ or PPARγ2 adenovirus. Mice were subjected to glucose tolerance (H) and insulin tolerance (I) tests on day 7 after adenoviral administration. Open and closed circles indicate SO-LacZ- and SO-PPARγ2-mice, respectively. Open and closed squares indicate HV-LacZ- and HV-PPARγ2-mice, respectively. Data are presented as mean±SD. **P<0.01 and *P<0.05 indicate HV-LacZ vs HV-PPARγ2-mice, and ## P<0.01 and # P<0.05 indicate HV-PPARγ2 vs SO-PPARγ2-mice, by unpaired t test.

Figure 5:
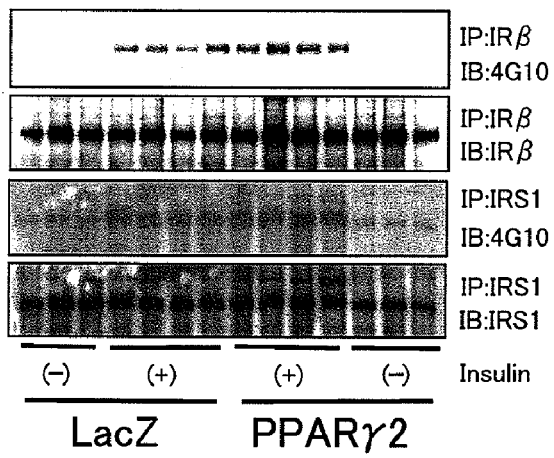
Figure 5:
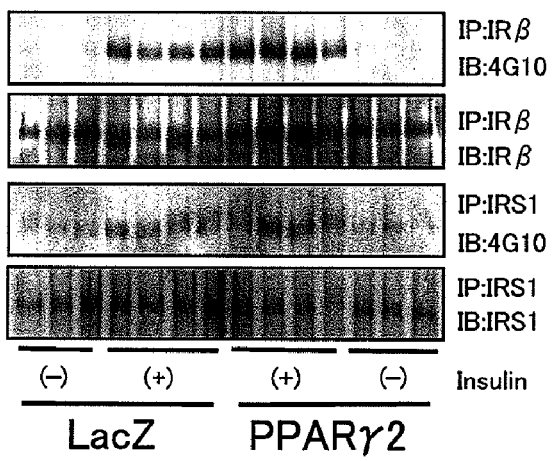
Figure 5:
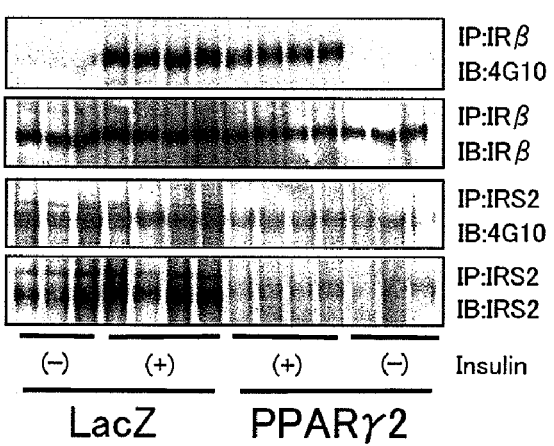

FIG. 5 shows insulin-stimulated tyrosine phosphorylation of insulin receptor (IR) and insulin receptor substrate (IRS) proteins in muscle, white adipose tissue and liver in an example. Seven days after adenoviral administration, mice fasted for 16 hours were injected intravenously with insulin or vehicle alone. Hindlimb muscles (A), epididymal fat (B) and the liver (C) were removed 300 sec later and lysates were immunoprecipitated with the indicated antibodies, followed by SDS-PAGE and immunoblotting with anti-phosphotyrosine antibody (4G10) or the individual antibody.

Figure 6:
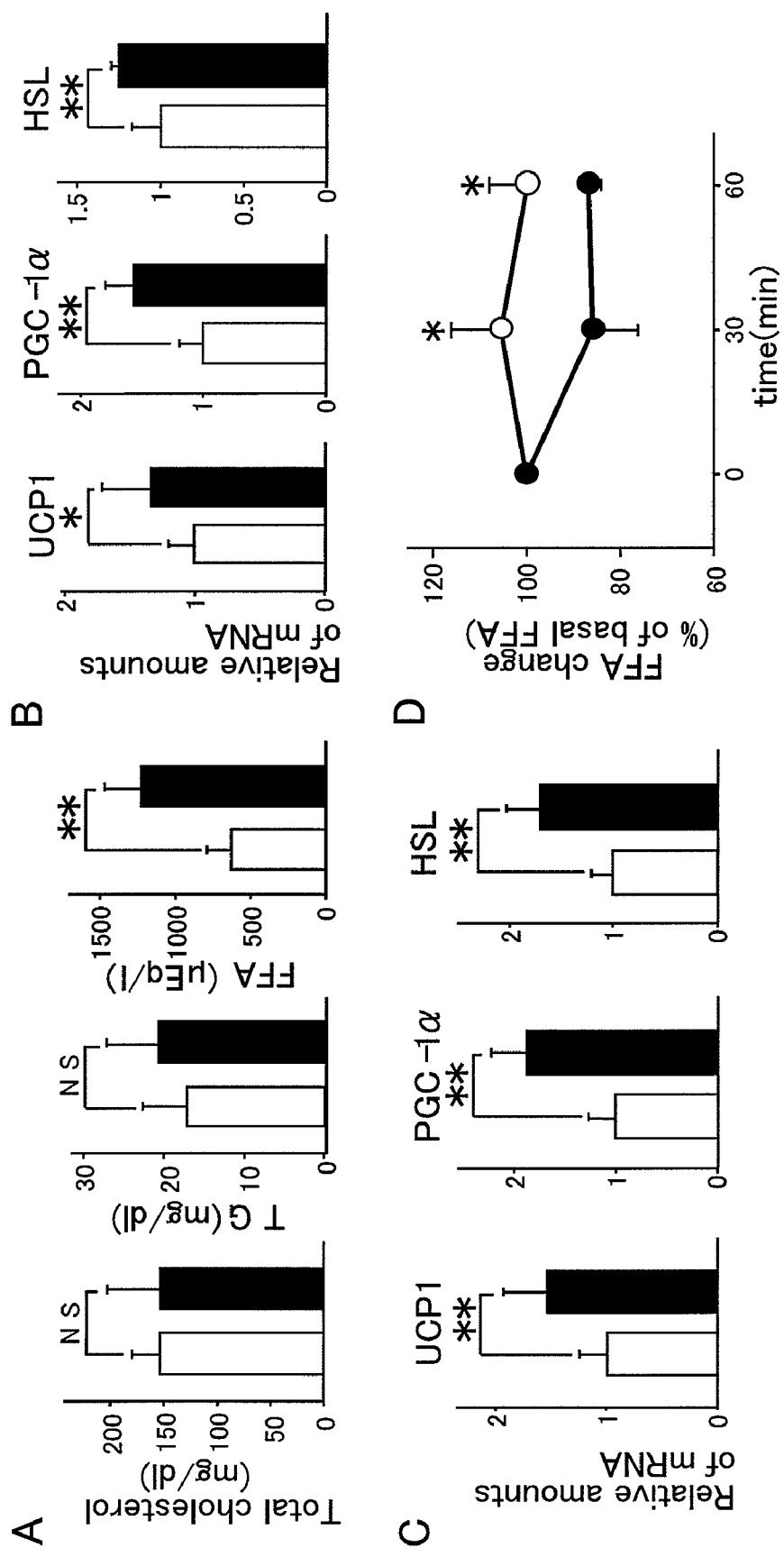

FIG. 6 shows sympathetic nerve activation involved in lipolysis in adipose tissue in an example. (A) Plasma lipid parameters (left: total cholesterol, middle: triglyceride (TG), right: free fatty acids (FFA)) in LacZ-mice (white bars) and PPARγ2-mice (black bars) on day 7 after adenoviral administration were measured in the 10 hour fasted state. (B-C) Relative amounts of UCP1 (left), PGC-1α (middle) and HSL (right) in brown adipose tissue (B) and epididymal fat tissue (C) from ad libitum-fed LacZ-mice (white bars) and PPARγ2-mice (black bars) on day 7 after adenoviral administration. (D) A pan-β adrenergic blocker, bupranolol, was injected intraperitoneally into LacZ-mice (open circles) and PPARγ2-mice (closed circles) in the fed state, on day 5 after adenoviral administration, followed by measurement of serum FFA levels. Data were expressed as percentages of serum FFA levels immediately before intraperitoneal bupranolol loading (10 mg/kg of body weight). Date are presented as mean±SD. **P<0.01 and *P<0.05, compared to control mice, by unpaired t test.

Figure 7:
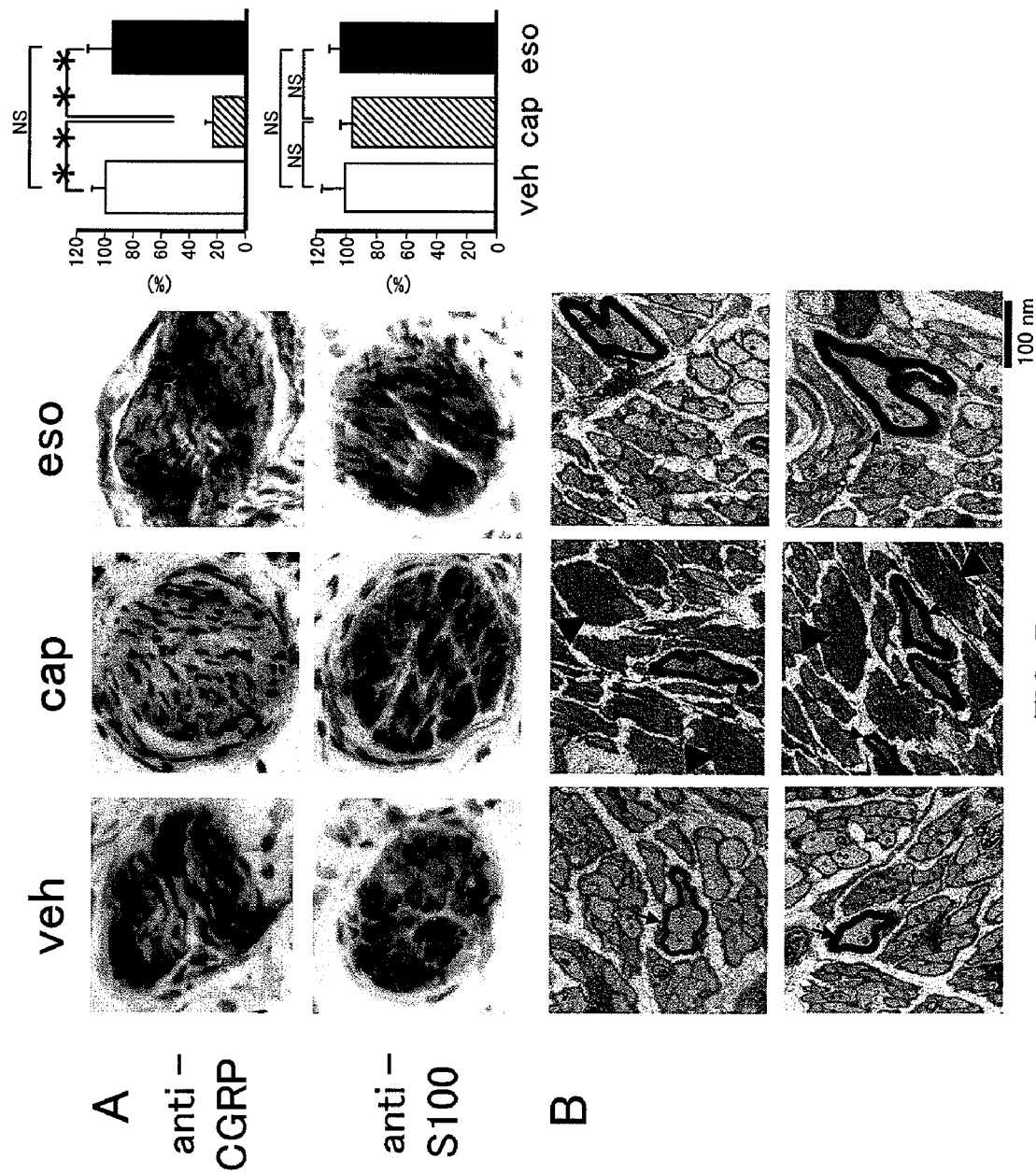

FIG. 7 shows damaged unmyelinated afferent vagal nerves by perivagal capsaicin application in an example. SD rats were treated with perivagal application of vehicle or capsaicin, 7 days prior to removal of the hepatic vagal nerves from vehicle-treated rats (veh) and capsaicin-treated rats (cap), and the esophgeal branch of the posterior vagal trunk from capsaicin-treated rats (eso). (A) Immunohistochemistry of the vagal nerves with anti-calcitonin gene-related peptide (CGRP) and anti-S100 antibodies. Magnification: ×400. The graphs show immunohistological staining intensities and the data are expressed as percentages of the intensities in vehicle-treated vagal nerve. (B) Transmission electron microscopy of the vagal nerves. While myelinated fibers are intact (arrows), unmyelinated fibers have been selectively degraded in perivagal capsaicin-treated nerves (arrowheads). Representative images from two rats of each group are shown.

Figure 8:
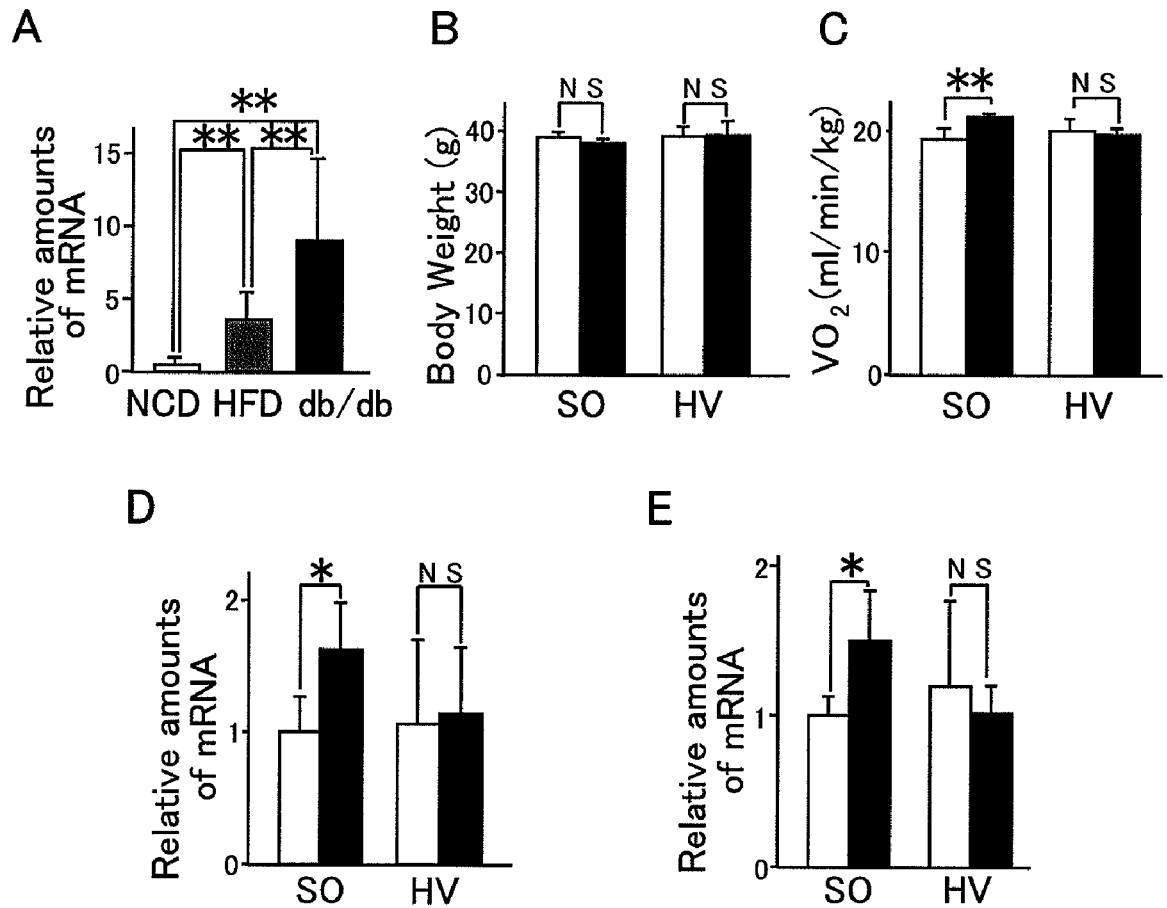

FIG. 8 shows thiazolidinedione (TZD)-enhanced energy expenditure in obese mice, which was inhibited by hepatic vagotomy, in an example. (A) Relative amounts of PPARγ2 mRNA in the livers of normal chow diet-fed (NCD) and high fat diet-fed C57BL/6 mice (HFD), and normal chow diet-fed db/db mice (db/db). (B-E) db/db mice were subjected to hepatic vagotomy (HV) or sham operation (SO) 7 days prior to 2-day administration of TZD (black bars) or vehicle (white bars), after which body weights (B) and resting oxygen consumptions (C) were measured. Relative amounts of UCP1 mRNA in BAT (D) and epididymal fat tissue (E) from mice in ad libitum-fed states. Data are presented as mean±SD. **P<0.01 and *P<0.05, compared to control mice, by unpaired t test.

Figure 9:
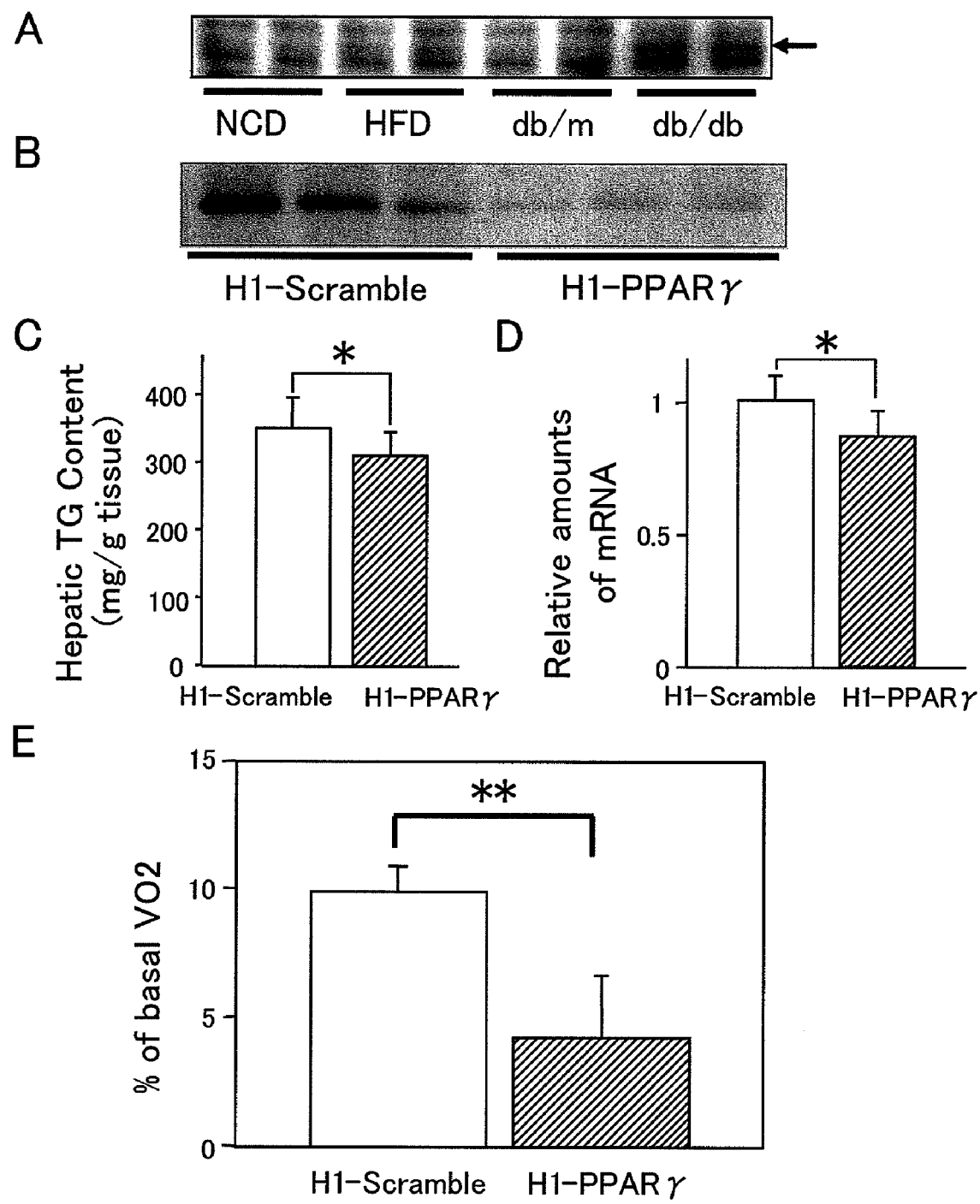

FIG. 9 shows TZD-enhanced energy expenditure inhibited by administration of recombinant adenovirus expressing shRNA for PPARγ. (A) Immunoblotting, with anti-PPARγ antibody, of liver extracts normal chow diet-fed (NCD) and high fat diet-fed (HFD) C57BL/6, normal chow diet-fed db/db and heterozygote control (db/m) mice. (B-E) db/db mice at 10 weeks of age were injected with recombinant adenovirus expressing shRNA for PPARγ (H1-PPARγ) or control scramble (H1-Scramble), 7 days prior to troglitazone administration (200 mg/kg of body weight) for 2 days, twice a day. On day 2, mice were sacrificed, following measurement of resting oxygen consumption. (B) Immunoblotting, with anti-PPARγ antibody, of liver extracts. (C) Hepatic triglyceride content. (D) Relative amounts of sterol regulatory element binding protein-1c mRNA in the liver. (E) Resting oxygen consumption was measured before and after (day 2) troglitazone administration. VO2 increments in response to the troglitazone treatment are expressed as percentages and presented as mean±SD. **P<0.01 and *P<0.05, compared to control mice, assessed by unpaired t test.

Figure 10:
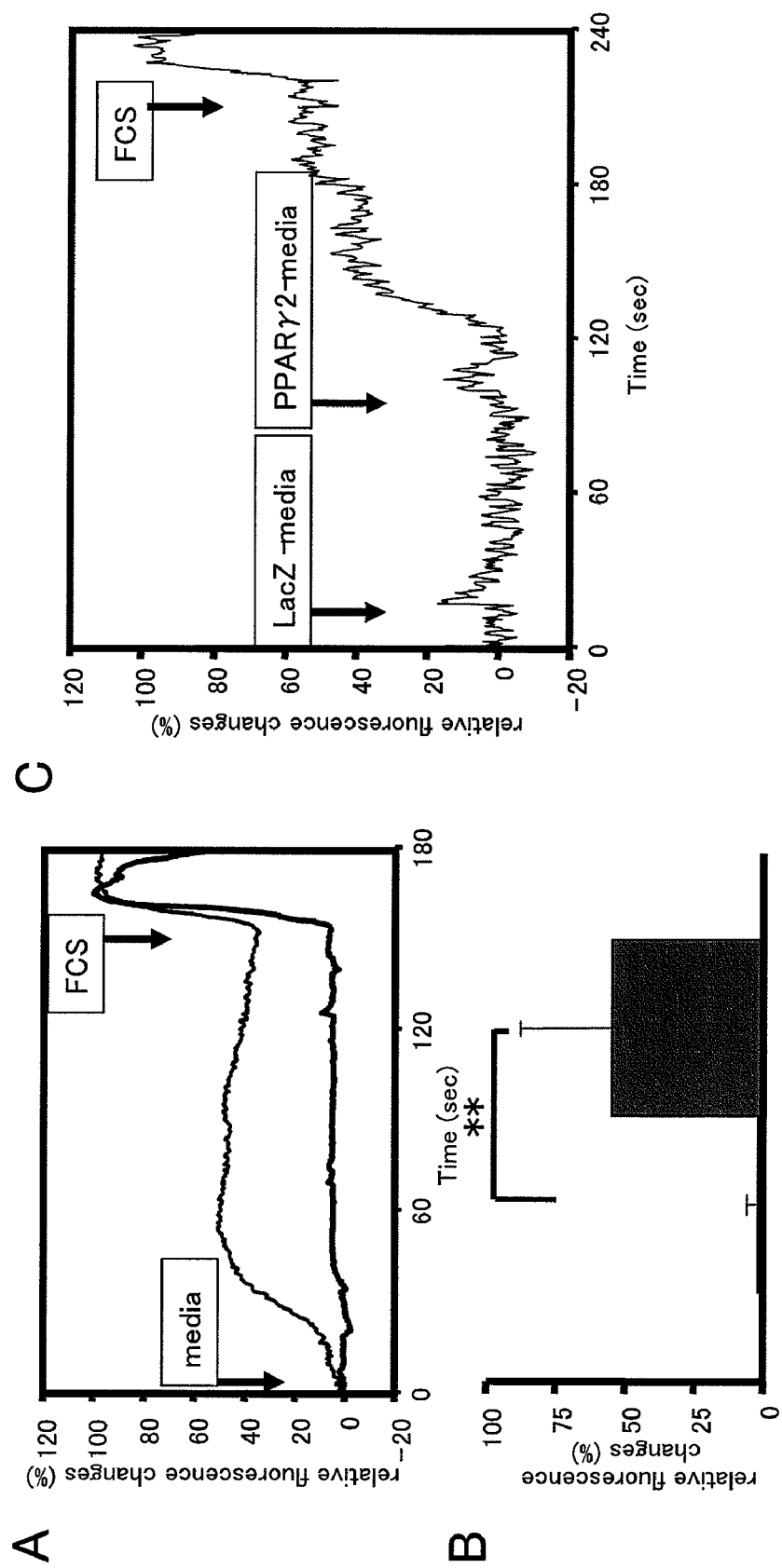

FIG. 10 shows relative changes in the free cytoplasmic calcium concentration in NGF-treated PC12 cells. (A) Relative fluorescence changes after LacZ-(blue) or PPARγ2-(red) media addition. The representative traces were created as a fluorescence ratio of the single Fluo4-loaded cell fluorescence. (B) The maximal ratio of fluorescence in NGF-treated PC12 cells after LacZ-(blue) or PPARγ2-(red) media addition. **P<0.01, compared to LacZ-media addition, by unpaired t test. (C) Responsiveness to successive additions of LacZ-media and PPARγ2-media in a single cell. The representative traces were created as a fluorescence ratio of the single Fluo4-loaded cell fluorescence. Data are presented as fluorescence change ratios in comparison with the fluorescence change of each cell after 10% FCS stimulation. Specifically, the fluorescence change for each cell after 10% FCS stimulation is 100 and the experimental data are presented as percentages.

DETAILED DESCRIPTION OF THE INVENTION

The object, characteristics, and advantages of the present invention as well as the idea thereof will be apparent to those skilled in the art from the descriptions given herein. It is to be understood that the embodiments and specific examples of the invention described herein below are to be taken as preferred examples of the present invention. These descriptions are only for illustrative and explanatory purposes and are not intended to limit the invention to these embodiments or examples. It is further apparent to those skilled in the art that various changes and modifications may be made based on the descriptions given herein within the intent and scope of the present invention disclosed herein.

Using adenovirus gene transfer, PPARγ2 was overexpressed specifically in the liver of mice or rats that have been fed by a high-fat food and their phenotype was analyzed. The PPARγ2-mice and PPARγ2-rats were analyzed in detail and involvement of a neuronal pathway in the cross-talk between the liver and adipose tissue was uncovered.

A selective hepatic vagotomy in the PPARγ2-mice, which involves dissection of both afferent and efferent vagal branches innervating the liver, completely blocked the decreases in WAT weights as well as WAT and BAT cell sizes and resting oxygen consumption. Further, application of a specific afferent neurotoxin, capsaicin, to the hepatic branch of the vagus of PPARγ2-rats completely blocked the hepatic PPARγ2 expression-induced decrease in WAT weight.

It was thus shown that afferent vagal nerve activation originating in the liver mediates the remote effects of hepatic PPARγ2 expression on peripheral lipolysis.

Furthermore, serum FFA levels were markedly increased in PPARγ2-mice, suggesting that hepatic PPARγ2 expression promotes hydrolysis of triglycerides stored in adipose tissues. Increased expression levels of the uncoupling protein (UCP)-1, PGC1α and hormone sensitive lipase in BAT and WAT indicate high tonus of sympathetic nerves innervating these adipose tissues. In addition, administration of a pan-β adrenergic blocker, bupranorol, decreased serum FFA in PPARγ2-mice.

It was thus shown that efferent sympathetic nerves to BAT and WAT enhances lipolysis in these adipose tissues in PPARγ2-mice.

These results indicate that stimulation of afferent vagal nerves from the liver mediates peripheral lipolysis in BAT and WAT via efferent sympathetic nerves. Embodiments of the present invention accomplished based on the above-described findings are hereinafter described in detail by giving Examples.

In an embodiment of the present invention, in order to activate efferent sympathetic nerves innervating adipose tissues, the afferent vagal nerve from the liver is stimulated. The stimulation can be done by enhancing PPARγ2 function in the liver through overexpression of the PPARγ2 gene or administration of a PPARγ2 agonist, but this specific embodiment is excluded from the scope of the present invention. In the present invention, the afferent vagal nerve from the liver is stimulated by other methods such as exciting physically the vagal nerve by electrical or magnetic devices or intraportal administration of fatty acids, but the stimulation methods are not limited thereto.

The stimulation of afferent vagal nerves from the liver results in diminishing adipose tissues such as BAT and WAT, increasing systemic energy expenditure such as oxygen consumption, suppressing weight gain or obesity, and/or an obesity-associated symptom. The obesity-associated symptom includes diabetes, hyperglycemia, glucose intolerance, and insulin resistance, but is not limited thereto.

The substances that excite the afferent vagal nerve from the liver are thus useful for diminishment of adipose tissues, or increasing systemic energy expenditure followed by reducing weight and/or improving obesity-associated symptoms. Such substances can be obtained by screening compound libraries or culture supernatants of hepatocytes in which PPARγ2 is overexpressed. Specifically, for example, a first screening can be performed by examining cytoplasmic calcium responses in neural cells to candidate substances. The neural cells used in this screening include neurons in primary culture, established neural cell strain or neurons differentiated in vitro, but are not limited thereto. Selected substances from the first screening may be applied to a second screening using in vivo. For example, each selected substance may be applied to the afferent vagal nerve from the liver and the responses at the efferent side may be examined.

Example 1

In Example 1, PPARγ2 was overexpressed in the livers of C57BL/6 mice using adenoviral gene transfer, and the effects on the afferent vagal and efferent sympathetic nerves and the phenotype due to the PPARγ2 overexpression were investigated.

After being fed a high-fat diet for 4 weeks, the mice developed obesity-associated diabetes (Y. Ishigaki et al., Diabetes 54, 322 (2005)). The PPARγ2 adenovirus vector was then administered intravenously (PPARγ2-mice). Control mice given the lacZ adenovirus (LacZ-mice) showed no alterations in blood glucose levels, food intake, or plasma lipid parameters after virus administration. Systemic infusion of the PPARγ2 adenovirus into mice resulted in expression of the transgene primarily in the liver (FIG. 1A), without increased expression in peripheral tissues including WAT (FIG. 1B).

The livers of PPARγ2-mice were pale and enlarged compared with those of control mice (FIG. 2A). Liver weights were significantly increased (FIG. 1C) due to increased triglyceride content (FIG. 1D). Histological analysis revealed an abundance of large lipid droplets in the livers of PPARγ2-mice without apparent inflammation or structural change (FIG. 2B). Thus, hepatic PPARγ2 expression induced severe hepatic steatosis. Hepatic PPARγ2 expression enhanced the expressions of lipogenesis-related genes (FIG. 3), indicating that increased uptake and synthesis of fatty acids induce severe steatosis.

Figure 1:
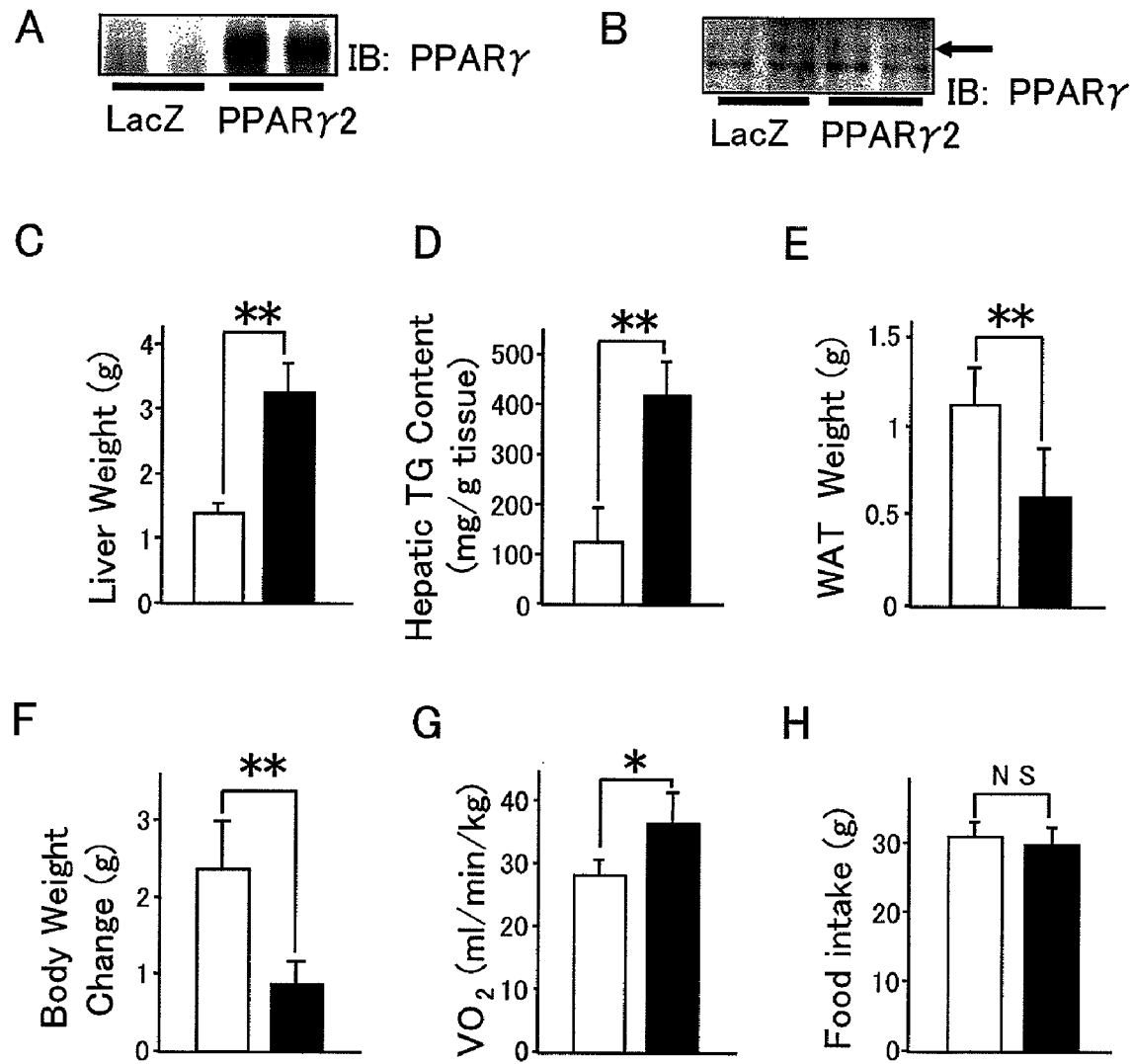
FIG. 1 shows the effect by hepatic PPARγ2 expression in an example, which aggravates hepatic steatosis but diminishes peripheral adiposity.

In contrast, WAT in PPARγ2-mice was remarkably diminished in size (FIG. 2A), e.g. epididymal fat weight was decreased by 46.6% in PPARγ2-mice versus controls (FIG. 1E). Cell diameters in WAT and BAT were also markedly decreased in PPARγ2-mice (FIG. 2C). The increases in body weights induced by a high fat diet were suppressed in PPARγ2-mice (FIG. 1F). Resting oxygen consumption was increased by 29.4% in PPARγ2-mice (FIG. 1G), while food intake did not differ from that of LacZ-mice (FIG. 1H). Thus, hepatic PPARγ2 expression increased systemic energy expenditure, thereby suppressing high fat diet-induced weight gain.

Control mice were hyperglycemic, hyperinsulinemic and hyperleptinemic in response to a 5-week high fat diet. Hepatic PPARγ2 expression decreased fasting blood glucose and insulin levels (FIG. 4A), indicating markedly improved systemic insulin sensitivity. As shown in FIG. 4B, PPARγ2-mice also showed a 79% reduction in serum leptin levels. Although serum adiponectin levels were similar to those in control mice, tumor necrosis factor (TNF)-α levels were significantly decreased in PPARγ2-mice. These findings are consistent with a reduction in peripheral adiposity.

Glucose tolerance (FIG. 4C) and insulin tolerance (FIG. 4D) tests showed that hepatic expression of PPARγ2 markedly improved insulin sensitivity and glucose tolerance. Furthermore, improved insulin sensitivity in muscle (FIG. 5A) and epididymal fat tissue (FIG. 5B) was confirmed by enhanced tyrosine phosphorylation of the insulin receptor and insulin receptor substrate-1 in response to insulin administration. Thus, hepatic PPARγ2 expression clearly exerts remote beneficial effects on insulin sensitivity in muscle and WAT. Although insulin sensitivity in the liver was impaired (FIG. 5C), hepatic PPARγ co-activator (PGC)-1α and hepatic phosphoenolpyruvate carboxykinase (PEPCK) expressions were decreased (FIG. 4E), indicating decreased hepatic glucose output.

To further examine insulin sensitivity and endogenous glucose production in PPARγ2-mice, we performed hyperinsulinemic euglycemic clamp experiments. Basal glucose production in PPARγ2-mice was decreased by 22% compared with that in LacZ-mice, while insulin's ability to suppress endogenous glucose production was severely blunted in PPARγ2-mice (FIG. 4F). In addition, glucose infusion rates in PPARγ2-mice were markedly increased (FIG. 4G). Thus, hepatic PPARγ2 expression improved insulin sensitivity in the periphery and decreased glucose output from the liver despite hepatic insulin resistance.

Serum FFA levels were markedly increased in PPARγ2-mice (FIG. 6A), indicating that hepatic PPARγ2 expression promotes hydrolysis of triglycerides stored in adipose tissues. Increased expression levels of UCP-1, PGC1α and hormone sensitive lipase in BAT (FIG. 6B) and WAT (FIG. 6C) indicate high tonus of sympathetic nerves innervating these adipose tissues. In addition, administration of bupranorol, a pan-β adrenergic blocker, decreased serum FFA in PPARγ2-mice, but had no effect in LacZ-mice (FIG. 6D), confirming that β adrenergic nerve function enhances lipolysis in adipose tissues of PPARγ2-mice.

To examine whether afferent nerves originating in the liver mediate the remote effects, we dissected the hepatic branch of the vagus. Seven days after selective hepatic vagotomy, we administered recombinant adenovirus encoding LacZ or PPARγ2. Hepatic PPARγ2 expression similarly altered liver weights, hepatic triglyceride content and PEPCK expression in mice subjected to hepatic vagotomy (HV-mice) and sham-operated mice (SO-mice) (Table 1). In contrast, selective hepatic vagotomy completely blocked the decreases in WAT weights and brown adipocyte size, and the increases in serum FFA, resting oxygen consumption and WAT UCP1 expression in PPARγ2-mice (Table 1), indicating that the hepatic vagus mediates the remote effects of hepatic PPARγ2 expression.

TABLE 1

|  | LacZ | PPARγ2 | P | LacZ | PPARγ2 | P |
|---|---|---|---|---|---|---|
|  | Sham operation | | | Hepatic vagotomy | | |
| Liver Weight (g) | 1.11 ± 0.13 | 2.30 ± 0.39 | <0.001 | 1.12 ± 0.07 | 2.07 ± 0.32 | <0.001 |
| Hepatic TG content (mg/g tissue) | 78.71 ± 46.5 | 171.26 ± 43.90 | 0.008 | 62.02 ± 24.92 | 215.09 ± 75.78 | <0.001 |
| PEPCK mRNA (Liver) | 1.00 ± 0.21 | 0.50 ± 0.17 | 0.003 | 1.356 ± 0.46 | 0.54 ± 0.22 | 0.002 |
| WAT Weight (g) | 1.13 ± 0.13 | 0.85 ± 0.14 | <0.001 | 1.04 ± 0.26 | 1.06 ± 0.19 | n.s. |
| BAT Cell Diameter (μm) | 11.55 ± 4.45 | 7.69 ± 2.09 | <0.001 | 10.63 ± 3.38 | 10.55 ± 3.93 | n.s. |
| FFA (μEq/l) | 556.14 ± 87.33 | 860.47 ± 206.04 | 0.005 | 533.14 ± 59.50 | 558.38 ± 151.58 | n.s. |
| VO₂ (ml/min/kg) | 30.25 ± 2.38 | 34.38 ± 3.03 | 0.015 | 32.73 ± 4.54 | 31.98 ± 4.05 | n.s. |
| UCP1 mRNA (WAT) | 1.00 ± 0.24 | 2.36 ± 0.77 | 0.019 | 2.05 ± 0.64 | 1.82 ± 1.15 | n.s. |
|  | Vehicle | | | Capsaicin | | |
| WAT Weight (g) | 8.95 ± 0.99 | 7.06 ± 1.32 | 0.024 | 8.70 ± 1.14 | 8.85 ± 1.71 | n.s. |

Table 1. Afferent vagal activation from the liver is involved in remote effects of hepatic PPARγ2 expression. (Upper Column) Mice were subjected to hepatic vagotomy or sham operation 7 days prior to administration of LacZ or PPARγ2 adenovirus. Resting oxygen consumption (VO2) was measured on day 3 after adenoviral injection. Mice were sacrificed after a 10 hour fast on day 7 after adenoviral injection. (Lower Column) Male SD rats with high fat diet-induced obesity were subjected to application of capsaicin or vehicle to the vagal hepatic branch 7 days prior to administration of LacZ or PPARγ2 adenovirus. Seven days after adenoviral administration, epididymal fat weights were determined. P values: compared to LacZ-mice, by unpaired t test. n.s.: not significant.

Hepatic vagotomy involves dissection of both afferent and efferent vagal branches innervating the liver. To determine whether the remote effects of hepatic PPARγ2 expression are mediated by the afferent vagus, we applied a specific afferent neurotoxin, capsaicin, to the hepatic branch of the vagus of diet-induced obese male SD rats. Seven days after perivagal application of capsaicin or vehicle, we administered recombinant adenovirus encoding LacZ or PPARγ2. Expression of calcitonin gene-related peptide, a sensory neuropeptide, was markedly decreased in the capsaicin-treated vagal nerve, while immunoreactivity for S100 proteins was similar in vehicle- and capsaicin-treated nerves (FIG. 7A). Furthermore, transmission electron microscopic analyses (FIG. 7B) revealed selective degradation of unmyelinated fibers in the vagal hepatic branch. In addition, capsaicin application to this branch did not affect the esophageal branch of the posterior vagal trunk (FIG. 7). These observations indicate selective de-afferentation of the hepatic branch of the vagus. Under these conditions, perivagal capsaicin treatment completely blocked the hepatic PPARγ2 expression-induced decrease in WAT weight (Table 1). Taken together, these findings indicate that afferent vagal nerve activation originating in the liver mediates the remote effects of hepatic PPARγ2 expression on peripheral lipolysis.

We next examined the effects of hepatic vagotomy on glucose (FIG. 4H) and insulin (FIG. 4I) tolerance test results in PPARγ2-mice. In SO-mice, glucose tolerance and insulin sensitivity were improved by hepatic PPARγ2 expression, but these improvements were partially suppressed by hepatic branch vagotomy. Hepatic PPARγ2 expression thus improved glucose tolerance and systemic insulin sensitivity via both improved peripheral insulin sensitivity and decreased hepatic glucose output; the former requires afferent vagal and efferent sympathetic nerves, while the latter does not.

Next, to determine whether the neuronal system, consisting of afferent vagal and efferent sympathetic nerves, functions in the physiological setting of enhanced endogenous PPARγ2 expression in the liver, we examined the effects of an antidiabetic TZD, a PPARγ agonist, using db/db mice, a murine model of genetic obesity and diabetes. In db/db mice, endogenous expression of PPARγ2, at both the mRNA (FIG. 8A) and the protein (FIG. 9A) levels, is markedly enhanced in the liver. To eliminate the secondary effects of body weight changes, troglitazone, a TZD derivative, was given to db/db mice for 2 days, followed by evaluation of acute effects. TZD administration for 2 days did not alter body weights (FIG. 8B), but did increase resting oxygen consumption (FIG. 8C) and UCP1 expression in BAT (FIG. 8D) and WAT (FIG. 8E), indicating activation of sympathetic nerves to BAT and WAT. Dissection of the hepatic branch of the vagus 7 days prior to TZD administration reversed the increases in resting oxygen consumption (FIG. 8C) as well as UCP1 expression in BAT (FIG. 8D) and WAT (FIG. 8E). These findings indicate that the neuronal pathway originating in the liver is also involved in the acute systemic effects of TZDs, under conditions in which hepatic PPARγ expression is up-regulated, such as in obese subjects.

To further examine whether endogenous PPARγ2 in the liver affects energy metabolism, we knocked down hepatic PPARγ in db/db mice. Administration of recombinant adenovirus expressing short hairpin RNA for PPARγ. (T. Hosono et al., Gene 348, 157 (2005)) 7 days prior to TZD treatment substantially decreased endogenous PPARγ expression in the liver (FIG. 9B) as well as hepatic triglyceride content (FIG. 9C) and sterol regulatory element binding protein-1c expression (FIG. 9D), indicating functional knockdown of hepatic PPARγ. Under these conditions, TZD-enhanced energy expenditure was partially but significantly suppressed (FIG. 9E). Thus, endogenous PPARγ in the liver was shown to regulate acute energy metabolism in vivo.

Example 2

In order to obtain a substance for weight reduction, a screening may be performed for a substance that excites the afferent vagal nerve from the liver. In this example, it was confirmed that a culture supernatant of hepatocytes in which PPARγ2 is overexpressed can be used as a source for the screening. For this purpose, cytoplasmic calcium responses to factors derived from such hepatocytes were examined in nerve growth factor (NGF)-treated PC12 cells as follows.

The Fao hepatoma cell line was infected with LacZ or PPARγ2 adenovirus, followed by incubation with Tyrode's solution for 6 h (LacZ-media and PPARγ2-media). Representative fluorescent changes after LacZ- or PPARγ2-media addition were shown in FIG. 10A. Substantial increases in cytoplasmic calcium concentrations (to levels that were at least 30% of those after 10% fetal calf serum stimulation) were observed in 74% of NGF-treated PC12 cells, while only slight or no responses were observed after LacZ-media. The maximal fluorescent ratios in NGF-treated PC12 cells were significantly greater after PPARγ2-media addition than LacZ-media addition (FIG. 10B). Successive additions of these media confirmed that, in 66% of NGF-treated PC12 cells, PPARγ2-media, but not LacZ-media, substantially increased cytoplasmic calcium concentrations (FIG. 10C). It was thus confirmed that factor(s) secreted from PPARγ2-expressing hepatocytes is involved in nerve excitation. Therefore, the culture supernatant of hepatocytes in which PPARγ2 is overexpressed can be used as a source for the screening by which a substance for weight reduction and/or diabetes therapy can be obtained.

Methods (1) Preparation of Recombinant Adenoviruses

Murine PPARγ2 cDNA was obtained by reverse transcriptase-polymerase chain reaction (RT-PCR) with total RNA obtained from 3T3-L1 adipocytes. Recombinant adenovirus, containing the murine PPARγ2 gene under the control of the CMV promoter, was prepared (H. Katagiri et al., J Biol Chem 271, 16987 (1996)). Recombinant adenovirus containing the bacterial β-galactosidase gene (Y. Kanegae et al., Nucleic Acids Res 23, 3816 (1995)) was used as a control.

(2) Animals

Animal studies were conducted in accordance with Tohoku University institutional guidelines. After 4 weeks of a high-fat diet (32% safflower oil, 33.1% casein, 17.6% sucrose, and 5.6% cellulose (S. Ikemoto et al., Proc Natl Acad Sci USA 92, 3096 (1995)) beginning at 5 weeks of age, body weight-matched male C57BL/6N mice were injected with adenovirus at a dose of $6.5 \times 10^7$ plaque forming units via the tail vein.

(3) Immunoblotting

Tissue samples were prepared as previously described (H. Ono et al., Diabetes 52, 2905 (2003)) and tissue protein extracts (250 μg total protein) were boiled in Laemmli buffer containing 10 mM dithiothreitol, then subjected to SDS-polyacrylamide gel electrophoresis. The liver lysates were immunoblotted with anti-PPARγ antibody (Santa Cruz Biotechnology, Santa Cruz, Calif., USA). The immunoblots were visualized with an enhanced chemiluminescence detection kit (Amersham, Buckinghamshire, UK).

(4) Hepatic Triglyceride Content

Frozen livers were homogenized and triglycerides were extracted with $CHCl_3:CH_3OH$ (2:1, v:v), dried and resuspended in 2-propanol. Triglyceride content was measured using Lipidos liquid (TOYOBO, Osaka, Japan).

(5) Oxygen Consumption

Oxygen consumption was determined with an $O_2/CO_2$ metabolism measuring system (MK-5000RQ, Muromachikikai, Tokyo, Japan) as previously described (Y. Ishigaki et al., Diabetes 54, 322 (2005)).

(6) Tyrosine Phosphorylation of Insulin Receptor (IR) and Insulin Receptor Substrates Mice fasted for 16 hours were injected with 200 μl of normal saline, with or without 10 U/kg body weight of insulin, via the tail vein. The liver, hindlimb muscle and epididymal fat tissue were removed 300 sec later and the homogenates were used for immunoprecipitation with anti-IR (Santa Cruz Biotechnology, Santa Cruz, Calif., USA), anti-IRS-1 (T. Ogihara et al., J Biol Chem 272, 12868 (1997)) or anti-IRS-2 antibody (Cell Signaling Technology, Beverly, Mass., USA) and then immunoblotted using antiphosphotyrosine antibody (4G10) or individual antibodies as described previously (T. Ogihara et al., J Biol Chem 272, 12868 (1997))

(7) Blood Analysis

Blood glucose was assayed with Antsense II (Horiba Industry, Kyoto, Japan). Serum insulin and leptin were determined with enzyme-linked immunosorbent assay kits (Morinaga Institute of Biological Science, Yokohama, Japan). Serum adiponectin and TNFα concentrations were measured with an ELISA kit (Ohtsuka Pharmaceutical Co. Ltd., Tokyo, Japan) and a TNFα assay kit (Amersham Biosciences, Uppsala, Sweden), respectively. Serum total cholesterol, triglyceride and free fatty acid concentrations were determined with Cholescolor liquid, Lipidos liquid (TOYOBO, Osaka, Japan), and NEFA C (Wako Pure Chemical Co., Osaka, Japan) kits, respectively.

(8) Hyperinsulinemic-Euglycemic Clamp

Hyperinsulinemic-euglycemic clamp studies were performed as described previously (J. R. Jones et al., Proc Natl Acad Sci USA 102, 6207 (2005)) with slight modification. Chronically cannulated, conscious and unrestrained mice on day 7 after adenovirus injection were fasted for 6 hours before the study. Each experiment consisted of a 60 min tracer equilibration period (−90 to −30 min), a 30 min control period (−30 to 0 min) and a 120 min clamp period (0 to 120 min). The tracers were infused through the jugular vein catheter. A priming dose of [3-$^3$H] glucose (5 μCi) was given at −90 min. Continuous infusions of [3-$^3$H] glucose were also started at −90 min at rates of 0.05 μCi/min. Insulin (10 mU/kg/min) was infused throughout the clamp study. Blood glucose was monitored every 5 min via carotid arterial catheter samples. Glucose was infused at a variable rate to maintain blood glucose levels at 100 mg/dl. Withdrawn erythrocytes were resuspended in sterile 0.9% saline and returned to the animal. Glucose infusion rates and endogenous glucose production were calculated as described (J. R. Jones et al., Proc Natl Acad Sci USA 102, 6207 (2005)).

(9) Glucose and Insulin Tolerance Tests and Bupranolol Loading Tests

Glucose tolerance tests were performed on mice fasted for 10 hours as previously described (Y. Ishigaki et al., Diabetes 54, 322 (2005)). Insulin tolerance tests were performed on ad libitum fed mice. Insulin (0.25 U/kg of body weight) was injected into the intraperitoneal space, followed by measurement of blood glucose. Bupranolol loading tests were performed on mice in the fed state. Serum FFA levels were measured immediately before and at 30 and 60 min after injection of intraperitoneal bupranolol (10 mg/kg of body weight, Kaken Pharmaceutical Co., Ltd. Tokyo, Japan).

(10) Quantitative RT-PCR-Based Gene Expression cDNA synthesized from total RNA was evaluated with a real time PCR quantitative system (Light Cycler Quick System 350S; Roche Diagnostics GmbH, Mannheim, Germany). The relative amount of mRNA was calculated with β-actin mRNA as the invariant control. The primers used are described in Table 2.

TABLE 2

| | No. | Forward (5' to 3') | No. | Reverse (5' to 3') |
|---|---|---|---|---|
| β-actin | 1 | TTGTAACCAACTGGGACGATATGG | 2 | GATCTTGATCTTCATGGTGCTAGG |
| PEPCK | 3 | AGCGGATATGGTGGGAAC | 4 | GGTCTCCACTCCTTGTTC |
| PGC-1α | 5 | ATACCGCAAAGAGCACGAGAAG | 6 | CTCAAGAGCAGCGAAAGCGTCACAG |
| UCP1 | 7 | TACCAAGCTGTGCGATGT | 8 | AAGCCCAATGATGTTCAGT |
| HSL | 9 | TGGTTCAACTGGAGAGCGGAT | 10 | TGATGCAGAGATTCCCACCTG |
| LDL-R | 11 | AGGGAATGAGGAGCAGCC | 12 | GTTCTTCAGCCGCCAGTT |
| FAT/CD36 | 13 | TGGCTAAATGAGACTGGGACC | 14 | ACATCACCACTCCAATCCCAAG |
| FATP2 | 15 | AGGGTCGAATTGGGATGGC | 16 | GGGTCACTTTGCGGTGTT |
| FATP5 | 17 | CTTCTACTTTCAAGACCGCCT | 18 | GGCACACCATAGACATTGACT |
| SREBP1c | 19 | CATGGATTGCACATTTGAAG | 20 | CCTGTGTCCCCTGTCTCA |
| MCAD | 21 | TCGAAAGCGGCTCACAAGCAG | 22 | CACCGCAGCTTTCCGGAATGT |
| FAS | 23 | TGCTCCCAGCTGCAGGC | 24 | GCCCGGTAGCTCTGGGTGTA |
| SCD1 | 25 | TGGGTTGGCTGCTTGTG | 26 | GCGTGGGCAGGATGAAG |
| LCAD | 27 | ATGCAAGAGCTTCCACAGGAA | 28 | CAGAAATCGCCAACTCAGCA |
| UCP2 | 29 | CATTCTGACCATGGTGCGTACTGA | 30 | GTTCATGTATCTCGTCTTGACCAC |
| PPARα | 31 | GGATGTCACACAATGCAATTCGC | 32 | TCACAGAACGGCTTCCTCAGGT |
| PPARδ | 33 | AACGCACCCTTTGTCATCCA | 34 | TTTCCACACCAGGCCCTTC |
| aP2 | 35 | GAATTCGATGAAATCACCGCA | 36 | CTCTTTATTGTGGTCGACTTTCCA |
| LXRα | 37 | GGATAGGGTTGGAGTCAGCA | 38 | CTTGCCGCTTCAGTTTCTTC |
| AMPK | 39 | TTTTTTGAAATGTGCGCCAGTC | 40 | AGCACGTAATACCGAGTGAGAT |
| SOCS3 | 41 | ACCAGCGCCACTTCTTCACG | 42 | GTGGAGCATCATACTGATCC |
| PPARγ2 | 43 | CGCTGATGCACTGCCTAT | 44 | AGAGGTCCACAGAGCTGATT |

(11) Dissection of Hepatic Branch of the Vagus

Seven days before adenovirus or troglitazone administration, mice were subjected to selective hepatic vagotomy (HV) or to sham operation (SO). A laparotomy incision was made on the ventral midline and the abdominal muscle wall was opened with a second incision. The gastrohepatic ligament was severed using fine forceps, and the stomach was gently retracted, revealing the descending ventral esophagus and the ventral subdiaphragmatic vagal trunk. The hepatic branch of this vagal trunk was then transected using fine forceps.

(12) Selective Blockade of Hepatic Vagal Afferent by Perivagal Application of Capsaicin After 4 weeks of a high-fat diet starting at 5 weeks of age, male SD rats were subjected to selective hepatic vagal afferent blockade. The hepatic branch of this vagal trunk was exposed as described above, then loosely tied with a cotton string immersed with or without capsaicin (Sigma Chemical Co, St Louis, Mo., USA) dissolved in olive oil (5% wt/vol). The cotton string was removed 30 min later and the abdominal incision was closed. Seven days after perivagal application of capsaicin or vehicle, recombinant adenovirus encoding LacZ or PPARγ2, at a dose of $6.5 \times 10^8$ plaque forming units (PFU), was injected via the tail vein.

(13) Histological Analysis

Livers, WAT and BAT were removed and fixed with 10% formalin and embedded in paraffin. Tissue sections were stained with hematoxylin eosin. Total adipocyte areas were traced manually. Brown and white adipocyte diameters were measured in 150 or more cells per mouse in each group. For vagal nerve immunohistochemistry, SD rats were anesthetized with pentobarbiturate (60 mg/kg), and then perfused transcardially with saline and sequentially with 4% paraformaldehyde in 0.2 M phosphate buffer (PB; pH 7.4). The vagal nerves were removed and chilled in 0.2 M PB with 30% sucrose. The streptavidin-biotin method was performed using a Histofine SAB-PO kit (Nichirei, Tokyo, Japan) for calcitonin gene-related peptide (Chemicon International, Temocula, Calif., USA) and S-100 protein (DAKO, Denmark). The antigen-antibody complex was visualized with 3,3'-diaminobenzidine and counterstained with heatoxylin. The intensities of bands were quantified with the NIH image 1.62 program.

(14) Transmission Electron Microscopic Analyses of Rat Vagal Nerves

Seven days after perivagal treatment with capsaicin or vehicle, nerves were fixed in 2.5% glutaraldehyde in 0.1 M sodium cacodylate buffer (pH 7.4), and postfixed in 1% osmium tetroxide. They were dehydrated in graded alcohols and embedded in Epon812. Ultrathin sections were stained with uranyl acetate and lead, and then examined under a transmission electron microscope (H-7600, Hitachi, Tokyo, Japan).

(15) TZD Administration by Gavage

Body weight matched db/db mice were divided into two groups at 10 weeks of age. One group was subjected to hepatic vagotomy, the other to sham operation. Seven days after the operations, each group of mice was divided into two subgroups, one of which received gastric gavage of troglitazone (200 mg/kg of body weight, Sankyo Co., Ltd. Tokyo, Japan) suspended in 0.5% carboxymethyl cellulose, twice a day, while the other received vehicle alone. On day 2, after measurement of resting oxygen consumption, mice were sacrificed and mRNA expression levels in adipose tissues were determined.

(16) RNA-Interference Experiments

Tail veins of 10-week-old db/db mice were injected with recombinant adenovirus encoding short-hairpin (sh) RNA for PPARγ (AdK7-H1-PPARγ) or shRNA for scramble (AdK7-H1-Scramble) (T. Hosono et al., Gene 348, 157 (2005)) at a dose of $5 \times 10^7$ PFU. Seven days after adenoviral administration, mice received gastric gavage of troglitazone (200 mg/kg of body weight) suspended in 0.5% carboxymethyl cellulose, twice a day. Resting oxygen consumption was measured before and after (day 2) troglitazone administration. After measurement of resting oxygen consumption on day 2, mice were sacrificed, followed by immunoblotting of hepatic lysates with anti-PPARγ antibody (Upstate, Charlottesville, Va., USA).

(17) Measurement of the Free Cytoplasmic Calcium Concentration in NGF-Treated PC12 Cells PC12 cells were seeded onto collagen-coated glass bottom dishes, followed by treatment with 100 ng/ml NGF for 5 days. Fao cells, which had been infected with LacZ or PPARγ2 adenovirus, were incubated with Tyrode's solution (125 mM NaCl, 5 mM KCl, 30 mM D-glucose, 25 mM HEPES, pH 7.4, 2 mM $CaCl_2$, 1 mM $MgCl_2$) for 6 h. The incubation solutions (LacZ-media and PPARγ2-media) were collected and added to NGF-treated PC12 cells which had been preloaded with Fluo-4 in Tyrode's solution. Imaging was performed with a FluoView FV1000 confocal microscope (Olympus, Tokyo, Japan). Relative changes in the free cytoplasmic calcium concentration were monitored by measurement of fluorescent levels at 488 nm (A. H. Nashat et al. Mol Cell Biol 23 4778 (2003)).

(18) Statistical Analysis

All data are expressed as mean±SD. The statistical significance of differences was assessed by the unpaired t test and one factor ANOVA.

What is claimed is:

1. A method for screening for a substance for weight reduction, comprising the steps of:
   screening for a substance that excites an afferent vagal nerve from the liver, wherein the substance is comprised in culture supernatant of a hepatocyte in which PPARγ2 is overexpressed; and
   examining if the substance can suppress weight gain or obesity in an animal.

2. A method for screening for a substance for improving an obesity-associated symptom, comprising the steps of:
   screening for a substance that excites an afferent vagal nerve from the liver, wherein the substance is comprised in culture supernatant of a hepatocyte in which PPARγ2 is overexpressed; and
   examining if the substance can suppress an obesity-associated symptom in an animal.

3. The method of claim 2, wherein the obesity-associated symptom is selected from the group consisting of diabetes, hyperglycemia, glucose intolerance, and insulin resistance.

4. A method for screening for a substance for increasing systemic energy expenditure, comprising the steps of:
   screening for a substance that excites an afferent vagal nerve from the liver, wherein the substance is comprised in culture supernatant of a hepatocyte in which PPARγ2 is overexpressed; and
   examining if the substance can increase systemic energy expenditure in an animal.

* * * * *